(12) United States Patent
Winek et al.

(10) Patent No.: US 12,083,316 B2
(45) Date of Patent: Sep. 10, 2024

(54) MEANS TO SWITCH BETWEEN MULTIPLE FLUID PATHWAYS VIA A SINGLE ACCESS POINT IN AN IMPLANTED FLUID SYSTEM

(71) Applicant: Medtronic, Inc., Minneapolis, MN (US)

(72) Inventors: Michael E. Winek, Minneapolis, MN (US); Lloyd V. Hansen, Hugo, MN (US); Daniel T. Billings, Murrieta, CA (US); Lucien Bell N. Solefack, Inver Grove Heights, MN (US); Lauren Barth, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 855 days.

(21) Appl. No.: 16/803,269

(22) Filed: Feb. 27, 2020

(65) Prior Publication Data
US 2021/0268176 A1    Sep. 2, 2021

(51) Int. Cl.
*A61M 5/142*    (2006.01)
*A61M 5/14*    (2006.01)
(Continued)

(52) U.S. Cl.
CPC ...... *A61M 5/14276* (2013.01); *A61M 5/1407* (2013.01); *A61M 5/16881* (2013.01);
(Continued)

(58) Field of Classification Search
CPC ............ A61M 5/14276; A61M 5/1407; A61M 5/16881; A61M 2205/3515;
(Continued)

(56) References Cited

U.S. PATENT DOCUMENTS 4,573,994 A     3/1986  Fischell et al.
5,167,615 A  *  12/1992  East ..................... A61M 27/006
                                                    604/9
(Continued)

FOREIGN PATENT DOCUMENTS

DE    102008003330 A1    7/2009
WO   WO 2013/052414 A2    4/2013

OTHER PUBLICATIONS

PCT Application No. PCT/US2021/070191 Search Report and Written Opinion dated Jul. 1, 2021, 12 pages.
(Continued)

*Primary Examiner* — James D Ponton
(74) *Attorney, Agent, or Firm* — Husch Blackwell LLP

(57) ABSTRACT

An implantable medical device configured to selectively permit access to a medicament reservoir or fluid pathway by way of at least one contactless key, including an implantable medical device having a medicament reservoir fluidly coupled to an access port via a first conduit and a second conduct via an access valve, and at least one contactless key configured to impart a magnetic field upon a portion of the implantable medical pump to manipulate the access valve between a first position fluidly coupling the medicament reservoir to the access port via the first conduit, and a second position fluidly coupling the medicament reservoir to the access port via the second conduit, and a third position isolating the medicament reservoir from the access port.

12 Claims, 10 Drawing Sheets

(51) Int. Cl.
  *A61M 5/168* (2006.01)
  *A61M 5/42* (2006.01)
(52) U.S. Cl.
  CPC ..... *A61M 5/427* (2013.01); *A61M 2205/3515* (2013.01); *A61M 2205/581* (2013.01); *A61M 2205/582* (2013.01); *A61M 2210/1003* (2013.01)
(58) Field of Classification Search
  CPC ...... A61M 2205/581; A61M 2205/582; A61M 2210/1003; A61M 2039/0238; A61M 2205/3523; A61M 2205/52; A61M 39/0208; A61M 5/42; A61M 5/427
  See application file for complete search history.

(56) References Cited

U.S. PATENT DOCUMENTS

| | | | |
|---|---|---|---|
| 5,217,442 A | 6/1993 | Davis | |
| 5,637,083 A | 6/1997 | Bertrand et al. | |
| 6,283,943 B1 | 9/2001 | Dy et al. | |
| 6,579,280 B1 | 6/2003 | Kovach et al. | |
| 6,805,687 B2 | 10/2004 | Dextradeur et al. | |
| 6,962,580 B2 | 11/2005 | Adams et al. | |
| 7,044,932 B2* | 5/2006 | Borchard | A61M 5/14276 604/116 |
| 7,072,802 B2 | 7/2006 | Hartlaub | |
| 7,255,682 B1* | 8/2007 | Bartol, Jr. | A61M 5/158 604/116 |
| 7,637,897 B2 | 12/2009 | Ginggen | |
| 7,942,863 B2 | 5/2011 | Kalpin et al. | |
| 8,535,280 B2 | 9/2013 | Rogers et al. | |
| 8,721,605 B2 | 5/2014 | Brandt et al. | |
| 9,122,785 B2 | 9/2015 | Alme et al. | |
| 9,421,325 B2 | 8/2016 | Kalpin | |
| 9,590,352 B2 | 3/2017 | Bilbrey et al. | |
| 2002/0022793 A1 | 2/2002 | Bertrand et al. | |
| 2003/0181888 A1 | 9/2003 | Dextradeur et al. | |
| 2004/0249334 A1 | 12/2004 | Cull | |
| 2005/0187515 A1* | 8/2005 | Varrichio | A61M 5/172 604/67 |
| 2006/0089619 A1 | 4/2006 | Ginggen | |
| 2006/0229548 A1 | 10/2006 | Cull | |
| 2006/0247737 A1* | 11/2006 | Olson | A61M 5/14276 607/33 |
| 2007/0255227 A1 | 11/2007 | Haase | |
| 2011/0068885 A1 | 3/2011 | Fullerton et al. | |
| 2012/0053514 A1* | 3/2012 | Robinson | A61M 5/1684 604/246 |
| 2013/0116665 A1 | 5/2013 | Humayun et al. | |
| 2014/0228765 A1 | 8/2014 | Burke et al. | |
| 2016/0015957 A1 | 1/2016 | Tieck et al. | |
| 2017/0043151 A1 | 2/2017 | Bellrichard et al. | |
| 2018/0154074 A1 | 6/2018 | Blomme et al. | |
| 2020/0121849 A1 | 4/2020 | Chrisenson et al. | |
| 2020/0121850 A1 | 4/2020 | Christenson et al. | |

OTHER PUBLICATIONS

Application and File History for U.S. Appl. No. 16/803,216, filed Feb. 27, 2020. Inventor: Winek.
Extended European Search Report for European Application No. 19202531.0, dated Jan. 27, 2020.

\* cited by examiner

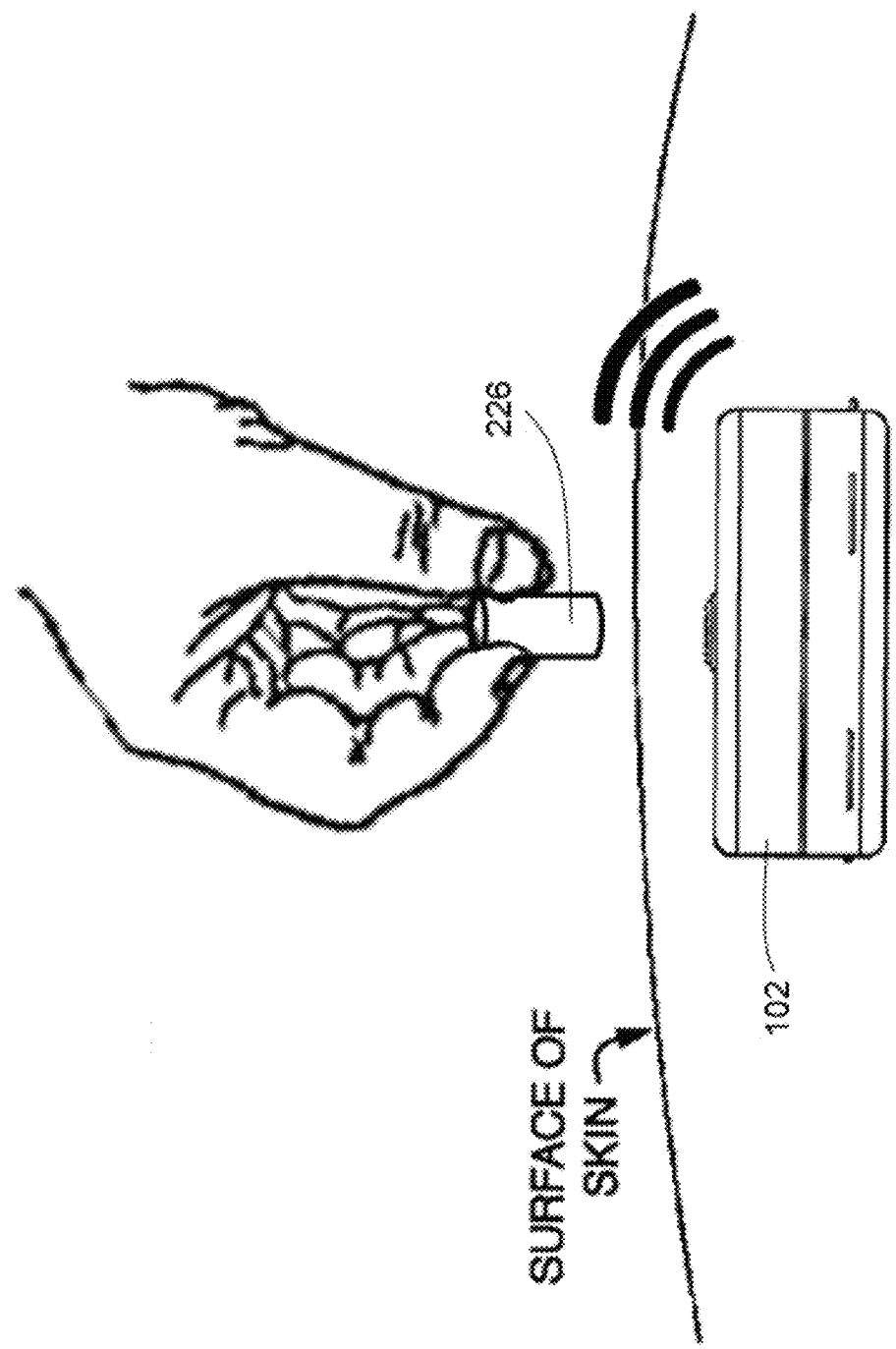

MEANS TO SWITCH BETWEEN MULTIPLE FLUID PATHWAYS VIA A SINGLE ACCESS POINT IN AN IMPLANTED FLUID SYSTEM

TECHNICAL FIELD

The present technology is generally related to implantable medical devices, and more particularly to implantable medical pumps and ports for managing the delivery and dispensation of prescribed therapeutic agents.

BACKGROUND

Implantable medical devices, such as implantable medical pumps and ports, are useful in managing the delivery and dispensation of prescribed therapeutic agents, nutrients, drugs, medicaments such as antibiotics, blood clotting agents, analgesics and other fluid or fluid like substances (collectively "medicaments" or "infusates") to patients in volume- and time-controlled doses as well as through boluses. Such implantable pumps and ports are particularly useful for treating diseases and disorders that require regular or chronic (i.e., long-term) pharmacological intervention, including tremor, spasticity, multiple sclerosis, Alzheimer's disease, Parkinson's disease, amyotrophic lateral sclerosis (ALS), Huntington's disease, cancer, epilepsy, chronic pain, urinary or fecal incontinence, sexual dysfunction, obesity, and gastroparesis, to name just a few. Depending upon their specific designs and intended uses, implantable pumps and ports are well adapted to administer infusates to specific areas within the vasculatures and central nervous system, including the subarachnoid, epidural, intrathecal, and intracranial spaces or provide access to those spaces for aspiration.

Providing access to the cerebrospinal fluid for the administration of infusates or aspiration of fluid has a number of important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. In addition, infusion of substances from outside the body requires a transcutaneous catheter or access with a hypodermic needle, which results in other risks such as infection or catheter dislodgment. Further, implantable pumps avoid the problem of patient noncompliance, namely the patient failing to take the prescribed drug or therapy as instructed.

Such implantable pumps and ports are typically implanted at a location within the body of a patient (typically a subcutaneous region in the lower abdomen) and are connected to a catheter configured to deliver medicament to a selected delivery site in the patient. The catheter is generally configured as a flexible tube with a lumen running the length of the catheter to a selected delivery site in the body, such as the intracranial or subarachnoid space.

Implantable medical pumps of this type often include an expandable fluid reservoir, which is accessible for refill or aspiration through an access port. Frequently, the pumps comprise more than one access port. For example, a first access port can be configured to provide access to a reservoir containing medicament for long-term, slow delivery, while a second access port can be configured to enable immediate bolus administration directly into the patient or to withdraw body fluids.

During the refill process, it is important that the medicament not be inadvertently injected directly into the body of the patient, as a potentially fatal overdose may occur. For example, if a large quantity of medicament intended for a reservoir refill (which is normally injected through the first port), is accidentally injected into the second port, the medicament would flow directly into the catheter resulting in an immediate delivery of the entire refill quantity. In another example, if the portion of the refilling apparatus employed to deliver the medicament is not properly positioned within the correct access port, the medicament can be injected directly into a pocket surrounding the implantable pump or port.

In addition to the problem of inadvertently injecting medicament into the wrong port, or directly into the patient, with medications having an abuse potential, such as morphine and fentanyl, the reservoir may be accessed through unauthorized or undesirable procedures to gain access to those medications.

Applicants of the present disclosure have developed systems and methods to address these concerns.

SUMMARY OF THE DISCLOSURE

The techniques of this disclosure generally relate to implantable systems and methods configured to selectively perform one or more functions in the presence of a contactless key. For example, in one embodiment, the contactless keys are configured to selectively enable access to an otherwise isolated medicament reservoir or fluid pathway. In other embodiments, one or more magnetic elements incorporated into a access template can be configured to magnetically align the access template with an implanted medicament pump or port beneath the patient's skin, thereby aligning an access port of the access template with a medicament reservoir access port of the implanted medical pump or port. For ease of discussion, embodiments of the present disclosure generally depict a valve that opens and closes and an implantable medical pump; however, the disclosures should not be considered limiting in this regard, as embodiments of the present disclosure also cover, for example, a valve or similar mechanism that controls flow directionally, an implantable infusion systems generally, including implantable ports.

One embodiment of the present disclosure provides an implantable medical system configured to selectively permit access to the medicament reservoir by way of at least one contactless key, the implantable medical system including an implantable medical pump and at least one contactless key. The implantable medical pump can include a medicament reservoir fluidly coupled to an access port via one or more conduit including an access valve configured to selectively isolate the medicament reservoir from the access port. At least one contactless key can be configured to impart a magnetic field upon a portion of the implantable medical pump to manipulate the access valve between a closed position isolating the medicament reservoir from the access port, and an open position fluidly coupling the medicament reservoir to the access port.

In one embodiment, the at least one contactless key can be configured to cause the access valve to shift from the closed position to the open position. In one embodiment, the access valve can be biased to the closed position in the absence of the magnetic field imparted by the at least one contactless key. In one embodiment, the magnetic field of the at least one contactless key interacts (at least one of directly or indirectly) with the access valve.

In one embodiment, the access valve includes at least one of a magnetic element or ferritic portion configured to interact with the at least contactless key, thereby enabling the at least one contactless key to directly manipulate the access valve between the closed position and the open position. In one embodiment, the access valve can be at least one of a flapper valve, ball valve, reed valve, duckbill valve, rotary valve, or poppet valve.

In one embodiment, the system can further include a magnetic sensing element configured to sense the magnetic field imparted by the at least one contactless key for manipulation of the access valve, thereby enabling the at least one contactless key to indirectly manipulate the access valve between the closed position and the open position. In one embodiment, the magnetic sensing element can be at least one of a reed switch, magnetic field sensor, micro-electromechanical systems (MEMS) device, Hall effect sensor, magneto diode, magneto transistor, AMR magnetometer, GMR magnetometer, MTJ magnetometer, magnetooptical device, MEMS (Lorenz force), MEMS electron tunneling, or MEMS compass.

In one embodiment, the implantable medical pump can be configured to provide at least one of an auditory or vibratory feedback response upon proper positioning of the at least one contactless key relative to the implantable medical pump as determined by the magnetic sensing element. In one embodiment, the implantable medical pump can include a first conduit adapted for refilling of the medicament reservoir or delivering a bolus of medicament and a second conduit adapted for aspiration of the medicament reservoir or therapy delivery location. In one embodiment, a first contactless key is configured to selectively open the first conduit, and a second contactless key is configured to selectively open the second conduit.

In one embodiment, the at least one contactless key is at least one of a standalone key or incorporated into an implantable medical pump template of a refill kit. In one embodiment, the implantable medical pump is configured to log a date and time of a sensed presence of the magnetic field of the at least one contactless key or the number of access attempts.

Another embodiment of the present disclosure provides an implantable medical port system configured to selectively permit access to the fluid pathway by way of at least one contactless key, the implantable medical port system including an implantable medical port and at least one contactless key. The implantable medical port can include one or more fluid pathways that are coupled to an access port via one or more conduit including an access valve configured to selectively isolate the access port from the rest of the fluid pathway.

Another embodiment of the present disclosure provides an implantable medical pump system configured to perform a desired function in the presence of a contactless key. The implantable medical pump system can include an implantable medical pump and at least one contactless key. The implantable medical pump can have a magnetic sensing element and a processor configured to sense the presence of a magnetic field to perform one or more preprogrammed functions in response to the sensed magnetic field. The at least one contactless key can be configured to impart a magnetic field upon a portion of the implantable medical pump, thereby causing the implantable medical pump to perform the one or more preprogrammed functions.

In one embodiment, the at least one contactless key can be at least one of a standalone key or incorporated into an implantable medical pump template of a refill kit. In one embodiment, the one or more preprogrammed functions can include at least one of manipulating a valve, initiating a bolus delivery of medicament, temporarily pause medicament delivery, or entering an MRI safe mode. In one embodiment, the processor is configured to initiate at least one of an auditory or vibratory feedback response upon proper positioning of the at least one contactless key relative to the implantable medical pump as determined by the magnetic sensing element. In one embodiment, the processor is configured to log a date and time of a sensed presence of the magnetic field of the at least one contactless key. In one embodiment, the at least one contactless key includes two or more maxels.

Another embodiment of the present disclosure provides a method of selectively permitting access to the medicament reservoir of an implanted medical pump or a fluid pathway of an implanted medical port by way of at least one contactless key, the method including positioning at least one contactless key in proximity to an implanted medical pump, the implanted medical pump including a medicament reservoir fluidly coupled to an access port via one or more conduit including an access valve configured to selectively isolate the medicament reservoir from the access port, the at least one contactless key configured to impart a magnetic field upon a portion of the implantable medical pump, thereby causing the access port to shift from a closed position isolating the medicament reservoir from the access port to an open position fluidly coupling the medicament reservoir to the access port.

Another embodiment of the present disclosure provides an implantable medical pump refill kit including a refill template having at least one magnetic element configured to impart a magnetic field upon a portion of an implanted medical pump to urge the refill template into a desired position with respect to the implanted medical pump to align an access port of the refill template with a medicament reservoir access port of the implanted medical pump.

In one embodiment, the refill template can include at least two magnetic elements configured to magnetically align the refill template with the implanted medical pump upon positioning of the refill template on the skin of a patient in proximity to the implanted medical pump positioned beneath the skin. In one embodiment, the refill template can include a denial surface including a periphery generally corresponding to a periphery of the implanted medical pump. In one embodiment, the refill template can further include one or more alignment features configured to confirm alignment with one or more corresponding palpable features of the implanted medical pump.

In one embodiment, at least one magnetic element of the refill template can further be configured to impart a magnetic field upon a portion of the implanted medical pump to manipulate at least one valve between a closed position isolating a medicament reservoir from the medicament reservoir access port of the implanted medical pump, and an open position fluidly coupling the medicament reservoir to the medicament reservoir access port of the implanted medical pump. In one embodiment, the at least one magnetic element of the refill template can further be configured to impart a magnetic field sensed by a magnetic field sensing element of the implanted medical pump.

Another embodiment of the present disclosure provides an implantable medical pump refill system configured to enable aided alignment of a refill template with an implanted medical pump. The implantable medical pump refill system can include an implantable medical pump and an implantable medical pump refill kit. The implantable medical pump can include a medicament reservoir access port. The implantable medical pump refill kit can include a refill template having at least one magnetic element configured to impart a magnetic field upon a portion of the implantable medical pump to urge the refill template into a desired position with respect to the implantable medical pump to align an access port of the refill template with the medicament reservoir access port of the implantable medical pump.

In one embodiment, the refill template can include at least two magnetic elements configured to magnetically align the refill template with the implantable medical pump. In one embodiment, the refill template can include a denial surface including a periphery generally corresponding to a periphery of the implantable medical pump. In one embodiment, the refill template can further include one or more alignment features configured to confirm alignment with one or more corresponding palpable features of the implantable medical pump.

In one embodiment, the implantable pump can include a medicament reservoir fluidly coupled to the medicament reservoir access port via one or more conduit including an access valve configured to selectively isolate the medicament reservoir from the medicament reservoir access port. In one embodiment, the at least one magnetic element of the refill template can be configured to impart a magnetic field upon a portion of the implanted medical pump to manipulate the access valve between a closed position isolating a medicament reservoir from the medicament reservoir access port, and an open position fluidly coupling the medicament reservoir to the medicament reservoir access port.

In one embodiment, the access valve includes a magnetic element or ferritic portion configured to interact with the at least one magnetic element, thereby enabling the at least one magnetic element to directly manipulate the at least one valve between the closed position and the open position. In one embodiment, the implantable medical pump can include a first conduit fluidly coupling the medicament reservoir with the medicament reservoir access port adapted for refilling of the medicament reservoir, and a second conduit fluidly coupling the medicament reservoir with the medicament reservoir access port adapted for aspiration of the medicament reservoir. In one embodiment, a first contactless key can be configured to selectively open the first conduit, and a second contactless key can be configured to selectively open the second conduit.

In one embodiment, the implantable pump can include a magnetic field sensor configured to sense a magnetic field of the at least one magnetic element of the refill template. In one embodiment, the magnetic sensing element is at least one of a reed switch, magnetic field sensor, micro-electromechanical systems (MEMS) device, Hall effect sensor, magneto diode, magneto transistor, AMR magnetometer, GMR magnetometer, MTJ magnetometer, magnetooptical device, MEMS (Lorenz force), MEMS electron tunneling, or MEMS compass. In one embodiment, the implantable medical pump can be configured to provide at least one of an auditory or vibratory feedback response upon proper positioning of the refill template relative to the implantable medical pump as determined by the magnetic sensing element. In one embodiment, the implantable medical pump can be configured to log a date and time of a sensed presence of the magnetic field of the at least one refill template.

Another embodiment of the present disclosure provides a method of aiding alignment of a refill template with an implanted medical pump or port, including positioning a refill template of an implantable medical refill kit in proximity to an implanted medical pump or implanted medical port, the implanted medical pump or implanted medical port including an access port, the refill template including at least one magnetic element configured to impart a magnetic field upon a portion of the implanted medical pump to urge the refill template into a desired position with respect to the implanted medical pump to align an access port of the refill template with the medicament reservoir access port of the implanted medical pump.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which:

FIG. 10 a depicts the interaction between a discrete coded magnetic key and an implanted medical pump, in accordance with an embodiment of the disclosure.

Figure 1:
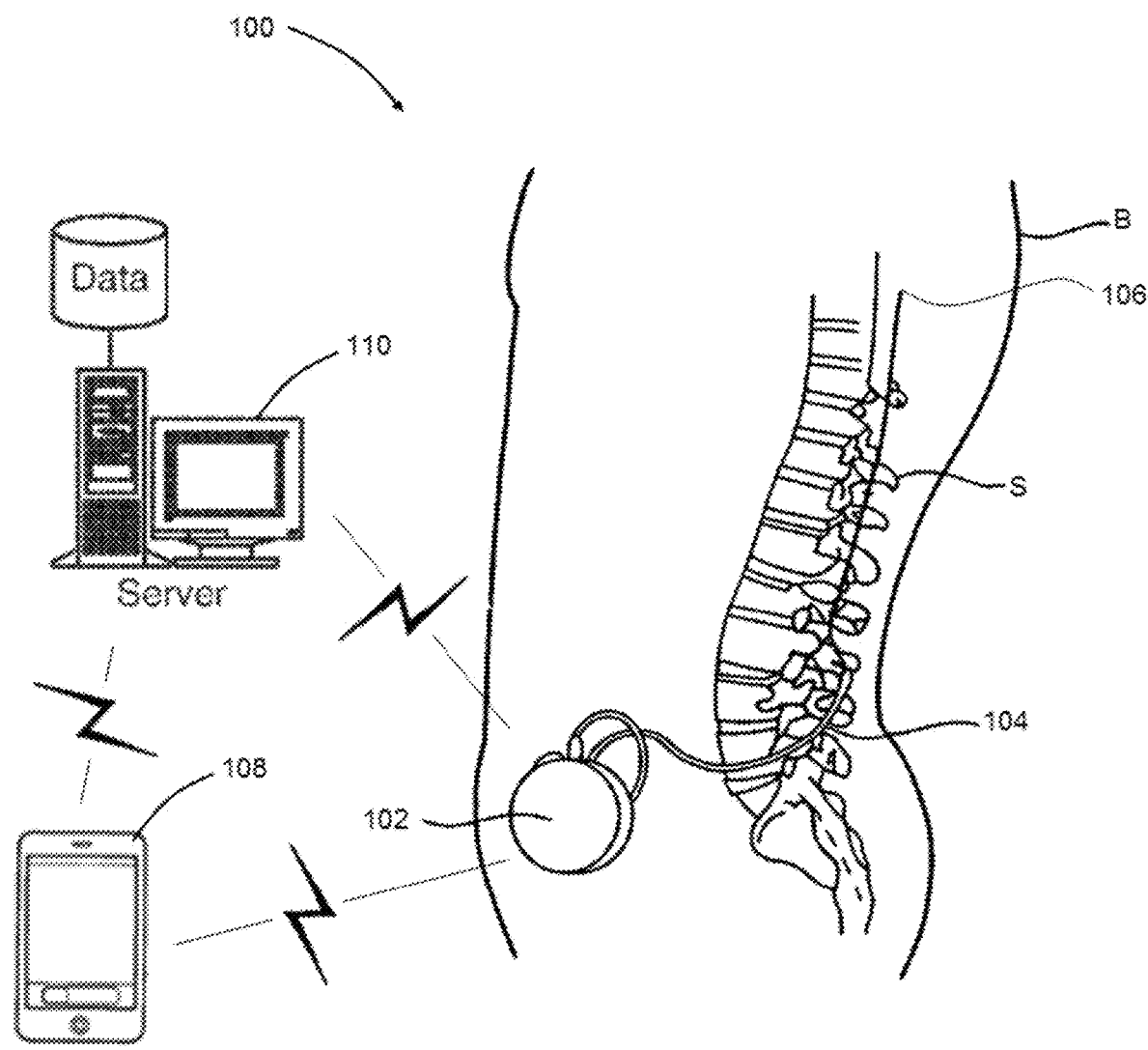
FIG. 1 is a schematic view depicting a medical delivery system, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 4:
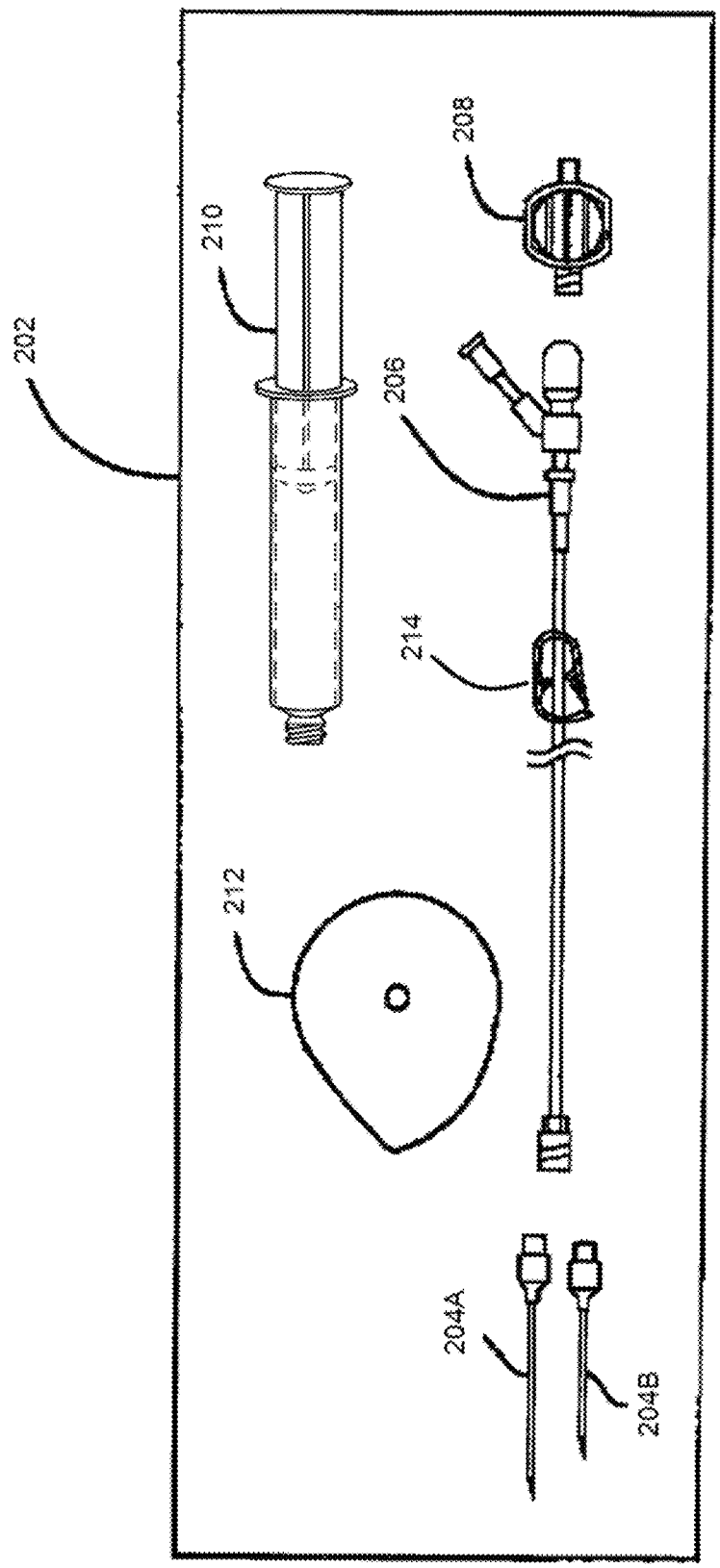
FIG. 4 depicts a refill kit for refilling or aspirating an implantable medicament pump or implantable port, in accordance with an embodiment of the disclosure.
Figure 6:
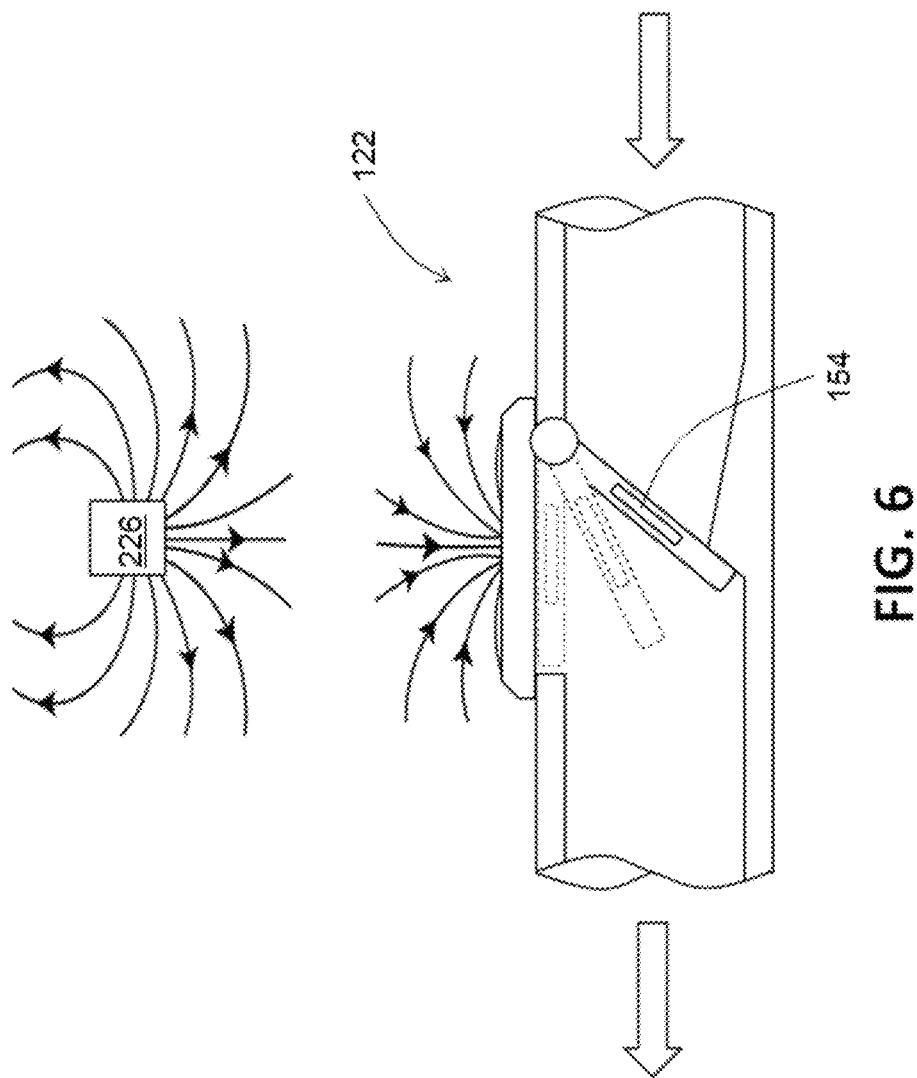
FIG. 6 depicts an interaction between an access valve and a contactless key, in accordance with a first embodiment of the disclosure.

Referring to FIG. 1, a schematic view of a medicament delivery system 100 configured to enable contactless manipulation of an access valve to fluidly couple an access port to a medicament reservoir is depicted in accordance with an embodiment of the disclosure. The medicament delivery system 100 can include an implantable medical pump 102 and a catheter 104. As depicted, the implantable medical pump 102 can be implanted within the body B of a patient, and can be in fluid communication with the catheter 104 having a distal tip 106 positioned within, for example, the subarachnoid space of the patient's spinal column S, thereby enabling intrathecal delivery of medicament through a lumen of the catheter 104. In other embodiments, the distal tip 106 can be positioned within the intracranial space, or other areas within the patient for targeted delivery of medicament. In one embodiment, the medical delivery system 100 can further include an optional external programmer 108 and an optional server 110 configured to communicate with the implantable medical pump 102, and with one another. In some embodiments, the medical delivery system 100 can optionally include a refill kit 202 (as depicted in FIG. 4). In some embodiments, the medical delivery system 100 can include a contactless key configured to impart a magnetic field upon a portion of the implantable medical pump 102 to manipulate an access valve between a closed position isolating a medicament reservoir from the access port, and an open position fluidly coupling the medicament reservoir to the access port (as depicted in FIG. 6).

Figure 2A:
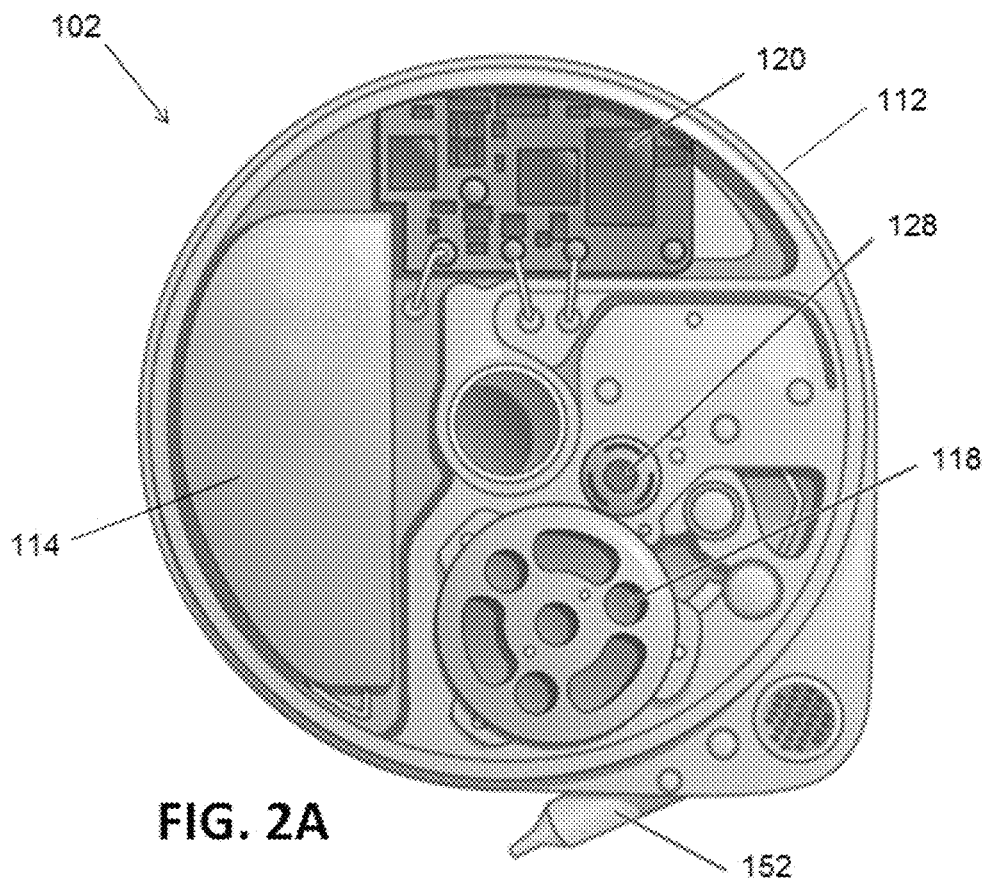
FIG. 2A is a cross-sectional schematic plan view depicting an implantable medicament pump, in accordance with an embodiment of the disclosure.
Figure 2B:
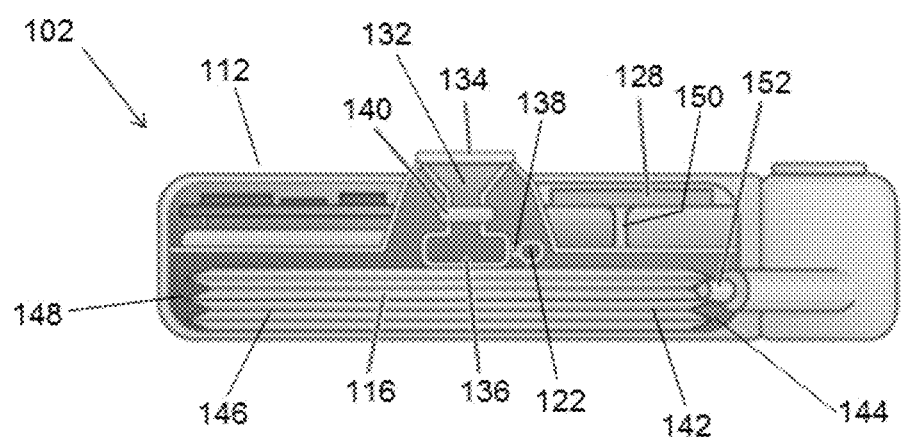
FIG. 2B is a cross-sectional schematic profile view depicting the implantable medicament pump of FIG. 2A.

Referring to FIGS. 2A-B, a cross-sectional views of an implantable medical pump 102 configured to enable contactless manipulation of an access valve to fluidly couple an access port to a medicament reservoir are depicted in accordance with an embodiment of the disclosure. Implantable medical pump 102 can generally include a housing 112, power source 114, medicament reservoir 116, medicament pump 118, and computing device 120. The housing 112 can be constructed of a material that is biocompatible and hermetically sealed, such as titanium, tantalum, stainless steel, plastic, ceramic, or the like.

Figure 7:
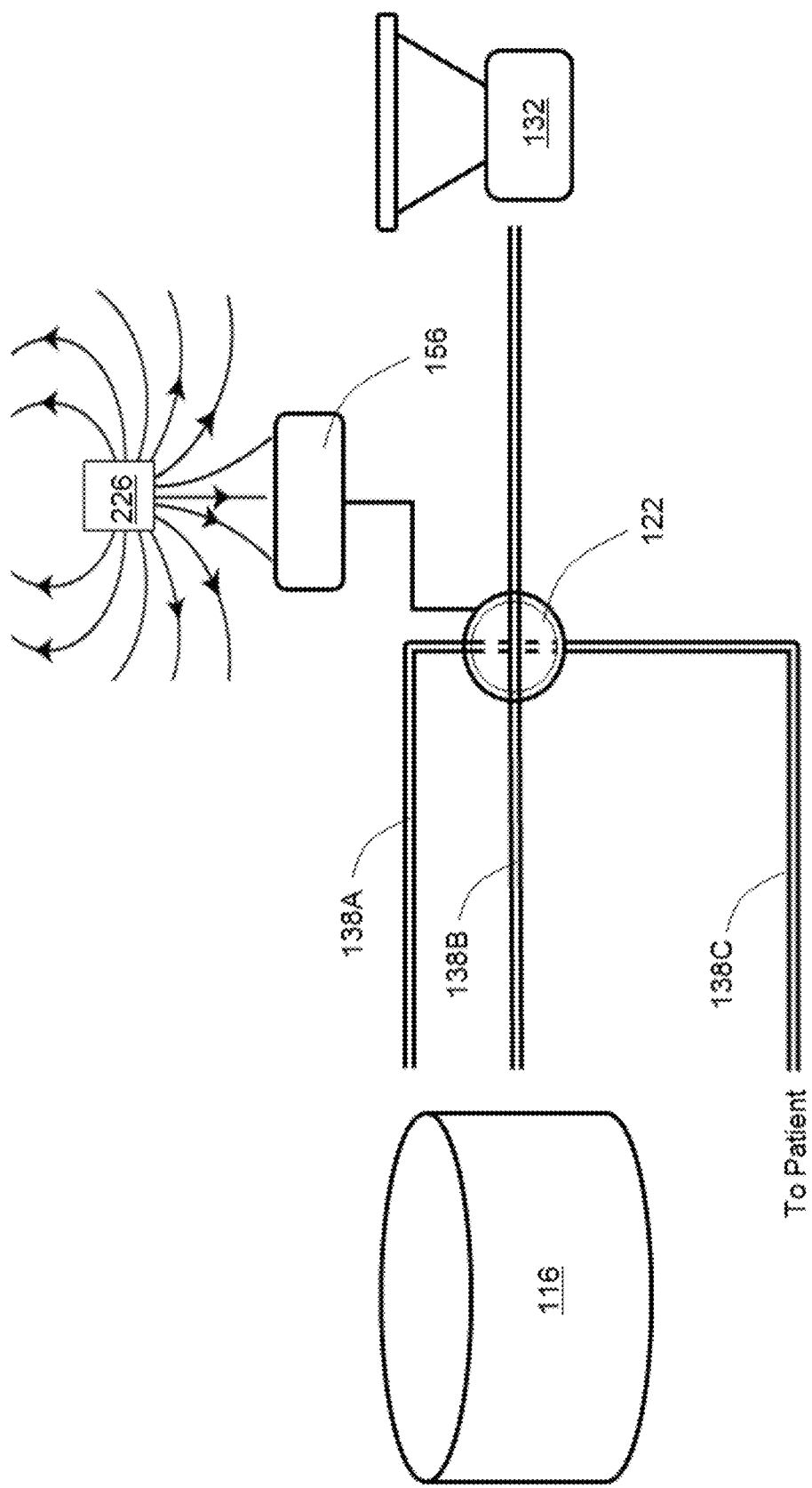
FIG. 7 depicts an interaction between an access valve and a contactless key, in accordance with a second embodiment of the disclosure.

The medicament reservoir 116 can be carried by the housing 112 and can be configured to contain medicament. In one embodiment, medicament within the medicament reservoir 116 can be accessed via an access port 132. Accordingly, the access port 132 can be utilized to refill, aspirate, or exchange the fluid within the medicament reservoir 116. In some embodiments, a refill kit 202, as depicted in FIG. 4, may be used to refill, aspirate, or exchange the fluid within the medicament reservoir 116. In some embodiments, the access port 132 can include a septum 134 configured to seal a port chamber 136 relative to an exterior of the housing 112. The self-sealing septum 134 can be constructed of a silicone rubber or other material having desirable self-sealing and longevity characteristics. The port chamber 136 can be in fluid communication with the medicament reservoir 116, for example via a conduit 138. In some embodiments, the conduit 138 can include an access valve 122 configured to selectively actuate to fluidly couple the port chamber and access port 132 with the reservoir 116. In some examples, a contactless key configured to impart a magnetic field upon a portion of the implantable medical pump 102 to manipulate access valve 112 between a closed position isolating medicament reservoir 116 from the access port 132, and an open position fluidly coupling the medicament reservoir 116 to the access port 132 (as depicted in FIG. 6). Depending upon the desired operation or for redundancy, in some embodiments, multiple conduits 138 (as depicted in FIG. 7) can fluidly couple the access port 132 to the reservoir 116 or the patient directly. In one embodiment, the access port 132 can further include an optional needle detection sensor 140, for example in the form of a mechanical switch or capacitive probe, configured to detect the presence of an injection needle of a refilling apparatus.

The medicament reservoir 116 can include a flexible diaphragm 142. The flexible diaphragm 142, alternatively referred to as a bellows, can be substantially cylindrical in shape and can include one or more convolutions 144 configured to enable the flexible diaphragm 140 to expand and contract between an extended or full position and an empty position. In one embodiment, the flexible diaphragm 142 can divide the medicament reservoir 116 into a medicament chamber 146 containing liquid medicament (within the flexible diaphragm 142), and a vapor chamber 148 (surrounding the flexible diaphragm 142).

The vapor chamber 148 surrounding the medicament chamber 146 can be configured to be filled with a fluorocarbon, such as Freon® 113 or other appropriate propellant, in a saturated vapor and liquid form. Over normal internal body temperatures, Freon 113 has a substantially linear pressure characteristic as it changes from liquid to vapor and vice versa. Therefore, at an essentially constant temperature within the human body (e.g., approximately 98.6° F.), the propellant within the vapor chamber 148 maintains substantially fixed pressure of around 19 psia (around +4.3 psig) regardless of the amount of medicament disposed within the medicament chamber 146.

As the medicament chamber 146 is filled with medicament, as hereinafter described, the flexible diaphragm 142 extends downwardly (with reference to FIG. 2B) toward a bottom portion of the housing 112 until it has reached a maximum volume or some other desired degree of fullness. Alternatively, as the medicament chamber 146 is aspirated, flexible diaphragm 142 contracts upwardly toward a top portion of the housing 112 until the medicament chamber reaches a minimum volume. In one embodiment, the flexible diaphragm 142 can have a compression spring rate which tends to naturally bias the flexible diaphragm 142 towards an expanded position. In particular, over the approximately 0.5 inch travel of the flexible diaphragm 142 between the expanded position and the empty position, the convolutions 144 can provide a linear compression spring rate configured to generally act against (but not completely counteract) the pressure within the vapor chamber 148.

In one embodiment, the implantable medical pump 102 can optionally include a fill sensor 150, for example in the form of an infrared (IR) transducer or other sensor configured to detect the expansion/contraction of the flexible diaphragm 142. Accordingly, the fill sensor 150 can be utilized to measure a dimension of the medicament reservoir 116 for the purpose of determining the volume of medicament therewithin.

The medicament pump 118 can be carried by the housing 112. The medicament pump 118 can be in fluid communication with the medicament reservoir 116 and can be in electrical communication with the computing device 120. The medicament pump 118 can be any pump sufficient for infusing medicament to the patient, such as a peristaltic pump, piston pump, a pump powered by a stepper motor, a pump powered by an AC motor, a pump powered by a DC motor, an electrostatic diaphragm, a piezoelectric motor, a solenoid, a shape memory alloy, or the like.

The catheter 104 can be operably coupled to the implantable medical pump 102 via catheter port 152, such that the lumen of the catheter 104 is in fluid communication with the medical pump 118 and reservoir 116. The distal tip 106 of the catheter 104 can be positioned in the subarachnoid space, intracranial space, or other areas within a patient, for targeted delivery of medicament.

Figure 3:
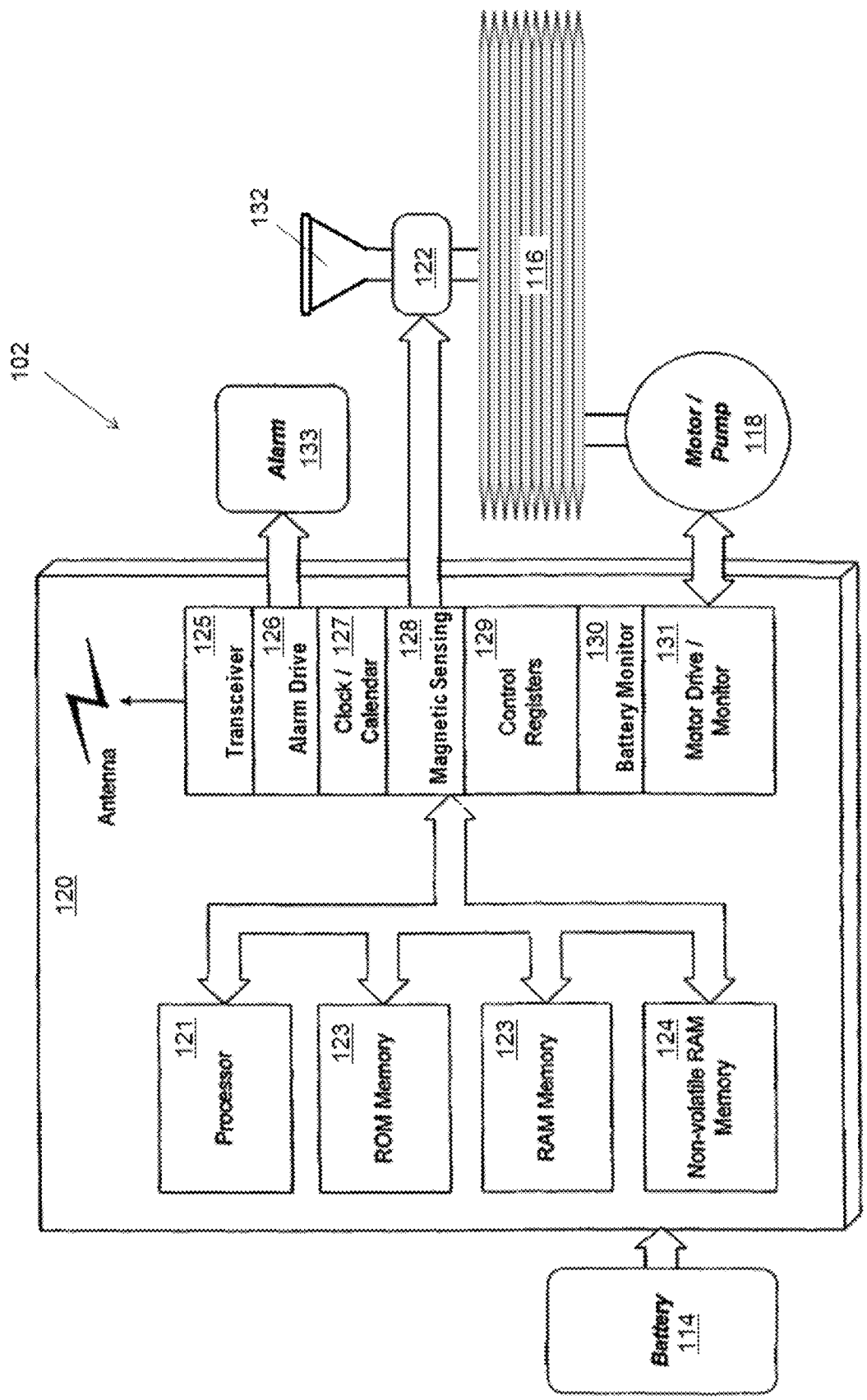
FIG. 3 is a schematic electrical diagram depicting an implantable medical pump, in accordance with an embodiment of the disclosure.

Referring to FIG. 3, a block diagram of an implantable medical pump 102 having structure configured to enable contactless manipulation of an access valve 122 to fluidly couple an access port 132 to a medicament reservoir 116 is depicted in accordance with an embodiment of the disclosure. The computing device 120 can be carried in the housing 112 (as depicted in FIG. 2A) and can be in electrical communication with one or more access valve 122, the medicament pump 118, and power source 114. The power source 114 can be a battery, such as a lithium-ion battery. The power source 114, which can be monitored via the battery monitor 130, can be carried in the housing 112, and can selectively operate the one or more access valve 122, medicament pump 118, and computing device 120. In some embodiments, the one or more access valve 122 can be in communication with a magnetic sensing element 128 configured to sense the presence of a contactless key or other magnetic element. Control of the medicament pump 118 can be directed by a motor drive/monitor element 131.

The computing device 120 can include a processor 121, memory 123/124, and transceiver circuitry 125. In one embodiment, the processor 121 can be a microprocessor, logic circuit, Application-Specific Integrated Circuit (ASIC) state machine, gate array, controller, or the like. The computing device 120 can be generally configured to control infusion of medicament according to programmed parameters or a specified treatment protocol. The programmed parameters or specified treatment protocol can be stored in the memory 123/124 for specific implementation by a control register 125. The transceiver circuitry 125 can be configured to receive information from and transmit information to the external programmer 108 and server 110. A clock/calendar element 127 can maintain system timing for the computing device 120. In one embodiment, an alarm drive 126 can be configured to activate one or more notification, alert or alarm features, such as an illuminated, auditory or vibratory alarm 133.

The implantable medical pump 102 can be configured to receive programmed parameters and other updates from the external programmer 108, which can communicate with the implantable medical pump 102 through well-known techniques such as wireless telemetry. In some embodiments, the external programmer 108 can be configured for exclusive communication with one or more implantable medical pumps 102. In other embodiments, the external programmer 108 can be any computing platform, such as a mobile phone or tablet. In some embodiments, the implantable medical pump 102 and external programmer 108 can further be in communication with a cloud-based server 110. The server 110 can be configured to receive, store and transmit information, such as program parameters, treatment protocols, drug libraries, and patient information, as well as to receive and store data recorded by the implantable medical pump 102.

Referring to FIG. 4, a filling/refilling/aspirating system or kit 202 configured for contactless interaction with a medical device via one or more magnetic elements is depicted in accordance with an embodiment of the disclosure. The kit 202 can be used to refill a medical device (such as an implantable medical pump 102 illustrated in FIGS. 2A-B) as further described below. In some embodiments, the kit 202 can include at least one needle 204A/B, an extension tubing set 206, filter 208, syringe 210, template 212, including at least one magnetic element configured to impart a magnetic field upon a portion of an implanted medical pump to urge the refill template into a desired position with respect to the implanted medical pump 102. For example, in some embodiments, the urge to the refill template 212 can be a forceable shifting of the refill template 212 into a desired position relative to the implantable pump 102, thereby aligning an access port of the refill template 212 with a medicament reservoir access port 132 of the implanted medical pump 102. In some embodiments, the kit 202 can further include an optional fenestrated drape (not depicted) and optional instruction manual (not depicted). In some embodiments, the kit 202 can include a first aspirating syringe provided to aspirate residual medicament from the medicament reservoir 116, and a second refill syringe provided to replenish the medicament reservoir 116. The extension tubing set 206 can include a proximal end connector configured to enable fluid coupling of the extension tubing set 206 to a discharge outlet of either syringe 210 or a discharge outlet of the filter 208.

A distal end connector of the extension tubing set 206 can form a luer lock configured to enable connection to the at least one needle 204. In other embodiments, the needle 204 can be preassembled with a distal end of the extension tubing set 206. The needle 204 is configured to operably penetrate the skin of the patient and enter the device 102 as further described below. A control valve (e.g., a tubing clamp 214) can also be provided. The tubing clamp 214 can be positioned along the extension tubing set 206 between the syringe 210 (or filter 208) and the medicament reservoir 116, and can be configured to move between an open position (wherein the tubing set 206 is open to enable a flow of fluid therein) and a closed position (wherein the tubing set 206 is closed or occluded such that flow is terminated).

Figure 5:
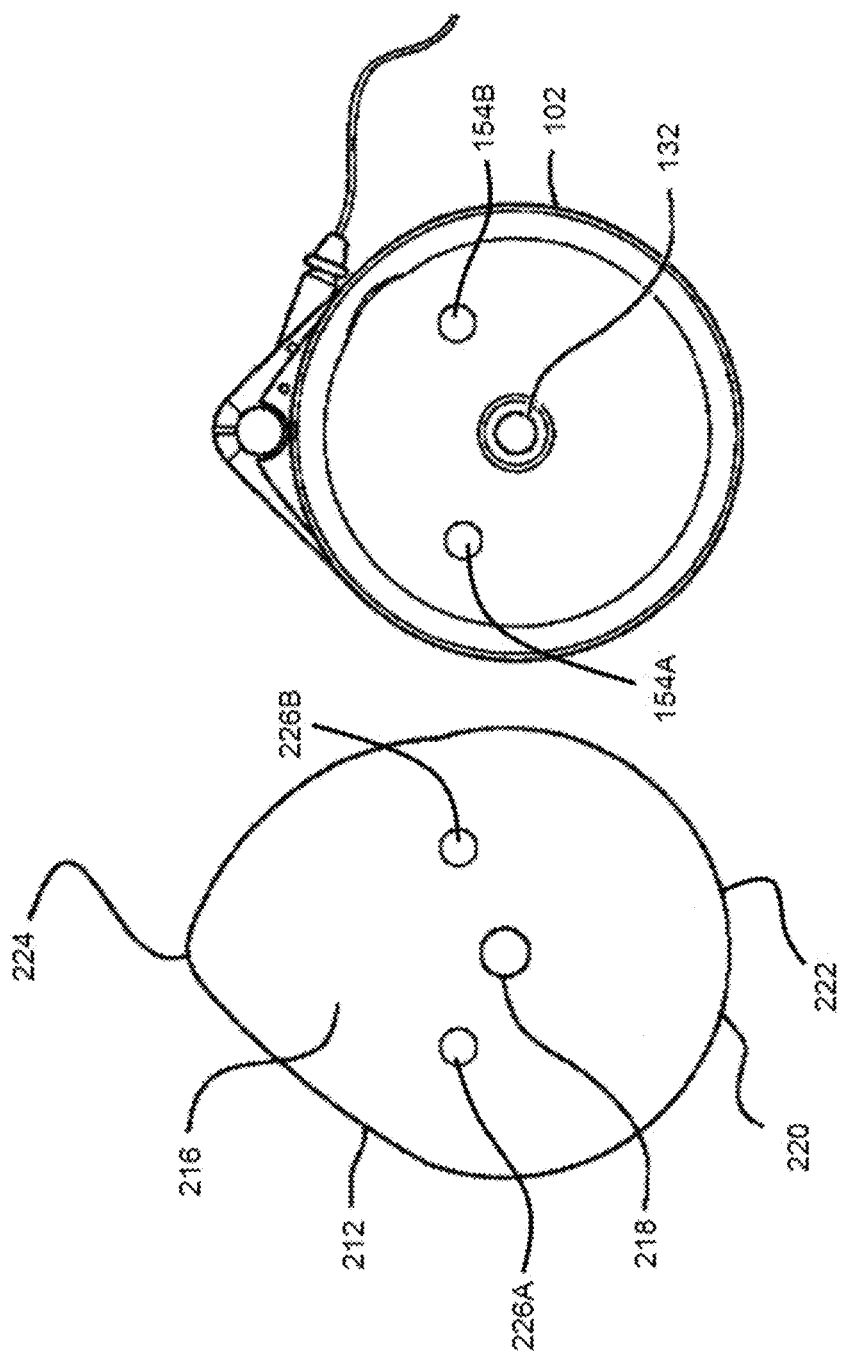
FIG. 5 depicts a refill template and implantable medical pump, in accordance with an embodiment of the disclosure.

With additional reference to FIG. 5, the template 212 can include a denial surface 216, an access port 218 and optional template labeling (not depicted). The denial surface 216 can include a periphery 220 with a location diameter 222 and one or more alignment feature 224. The denial surface 216 can be configured to inhibit penetration through a dermal layer and can be made of a polycarbonate or any other material configured to inhibit needle penetration through the denial surface 216 and into the dermal layer. The access port 218 is configured to permit penetration through the dermal layer, and generally serves as a user aid in properly locating the access port 132 of the implantable medical pump 102.

In some embodiments, the template 212 can further include an alignment feature 224. An alignment feature 224 can be any detail of the denial surface 216 enabling a user to correctly position the template 212 over the implantable medical pump 102, thereby aligning the access port 218 of the template 212 with the access port 132 of the implantable medical pump 102. For example, an alignment feature 224 can be represented as a deviation of the denial surface 216 from a circular shape to indicate that such a deviation portion should be aligned with a corresponding portion of the implantable medical pump 102 that deviates from a circular shape (in those cases in which the pump 102 is not perfectly circular).

In another embodiment, the alignment feature can be in the form of one or more magnetic elements 226A/B having a magnetic field strength and polarity configured to interact with a corresponding one or more magnetic elements 154A/B operably coupled to the implantable medical pump 102, thereby further serving as an aid to a user in magnetically aligning the access port 218 of the template 212 with the access port 132 of the implantable medical pump 102. Accordingly, the one or more magnetic elements 154, 226 can serve as a landmark in alignment of the template 212 with the medical pump 102, which in addition to locating access ports 132, can be useful in locating thermal sensors to adjust the rate of recharging or improving wireless communication systems. Although the template 212 is depicted as having two magnetic elements 226A/B, a greater or lesser number of magnetic elements is also contemplated. Additionally, the magnetic elements 226 can be positioned at any one or more locations of the template 212 and can be of different shapes and sizes for interaction with magnetic sensing elements 122 positioned at any one or more corresponding locations within the implantable medical pump 102.

In some embodiments, one or more magnetic elements 226, either operably coupled to the template 212 or generally held in proximity to the implantable medical pump 102 during a refill/aspiration procedure, can be configured directly or indirectly manipulate the access valve 122, thereby opening or closing the fluid connection between the access port 132 and a medicament reservoir 116 or fluid pathway. For example, with reference to FIG. 6, in one embodiment, the access valve 122 can include a corresponding magnetic element 154 or ferritic portion, such that a magnetic element 226 of the template 212 imparts a magnetic field having a strength and polarity sufficient to cause the corresponding magnetic element 154 of the access valve 122 to shift or pivot, thereby opening or closing the access valve 122. In this manner, the magnetic element 226 can act as a "contactless key" (alternatively referred to as a "magnetic key") configured to enable access to the reservoir 116. Although FIG. 6 depicts a flapper valve 122 being opened by a magnetic key 226, the valve 122 can also be configured to close when subjected to a magnetic field, thereby selectively isolating the access port 132 from the medicament reservoir 116. Additionally, other types of valves can be utilized; for example, the access valve can be an annular flapper valve, ball valve, reed valve, duckbill valve, rotary valve, or poppet valve, among other suitable valves.

With reference to FIG. 7, in other embodiments, manipulation of the access valve 122 via the one or more magnetic elements 226 can be indirect. For example, in some embodiments, the implantable medical pump 102 can include a magnetic sensing element 156 in communication with the access valve 122, for example via processor 121 (as depicted in FIG. 3). Suitable magnetic sensing elements 156 can include any device for detecting and measuring magnetic fields, such as a reed switch, magnetic field sensor, a microelectromechanical systems (MEMS) device, Hall effect sensor, magneto-diode, magneto-transistor, AMR magnetometer, GMR magnetometer, MTJ magnetometer, magneto-optical device, MEMS (Lorenz force), MEMS (electron tunneling), or MEMS compass, among other suitable sensing devices.

In some embodiments, the magnetic element 226 can be configured to impart a magnetic field having a strength and polarity sufficient to create a signal received by the magnetic sensing element 156, which in turn directs the access valve 122 to fluidly couple the access port 132 to the medicament reservoir 116 via one or more conduits 138A-C. For example, in one embodiment, the magnetic element 226 can have a magnetic field strength of about 100 gauss or greater, with either a positive or negative polarity; although magnetic field strengths of less than 100 gauss are also contemplated. Although FIG. 7 depicts a rotary valve 122 configured to enable the selection of three distinct pathways 138A-C, other types of valves 122 and other quantities of pathways 138A-C are also contemplated.

Accordingly, embodiments of the present disclosure may add additional levels of safety to inhibit unintended or accidental access of implanted fluid pathways by isolating one or more access points (e.g., access port 132) from the other components (e.g., reservoir 116) of the implanted system 102. Further, by enabling a user to select one of a number of different pathways 138A-C, the contactless key 226 may enable the user to differentiate between types of injections or differentiate between aspiration and injection, thereby enabling different pathways 138A-C to be specialized or otherwise tailored for different fluids, different processing (e.g., filtered versus non-filtered), or to provide redundancy. In some embodiments, the contactless key 226 may mitigate possible unauthorized access, or even to restrict access to the reservoir altogether.

In the past, various efforts have been made to alert healthcare providers to possible unauthorized access of the medicament reservoir 116. For example, in some cases, the implantable medical pump 102 would include a needle detection sensor configured to detect when a needle had been inserted into the access port. The event would be recorded by the pump, which could later be reviewed by a clinician. Accordingly, although such measures alerted healthcare providers to the possibility of unauthorized access after the fact, these measures did nothing to inhibit unauthorized access. By contrast, the use of a contactless key 226 to manipulate an access valve 122 to block a fluid path between the access port 132 and medicament reservoir 116 directly inhibits unauthorized access to the medicament reservoir.

In other cases, in an effort to restrict access to the medicament reservoir, the pump would be implanted with the access port facing inward, towards from the patient's skin. Naturally, implanting the pump in this configuration restricts a healthcare provider's ability to refill the pump at a later time. By contrast, the contactless key 226 can provide for an outward facing access port, while still controlling access to the port. In yet other cases, contactless key 226 may eliminate the need for a movable shutter attached to an exterior of the pump to physically block entry of a needle into the access port. Because the addition of a movable shield may increase the overall size of the implantable pump and reduce the battery life of the pump, contactless key 226 may improve power consumption and/or form-factor specifications for a pump in accordance with this disclosure. Furthermore, mechanical assemblies such as movable shields, may increase the likelihood of an inadvertent breakdown, which may result in a nonoperational shutter obscuring the access port, thereby permanently preventing healthcare providers from performing refill or aspiration procedures. Embodiments this disclosure may avoid various deficiencies in such mechanical assemblies altogether by using a contactless key 226.

Figure 8:
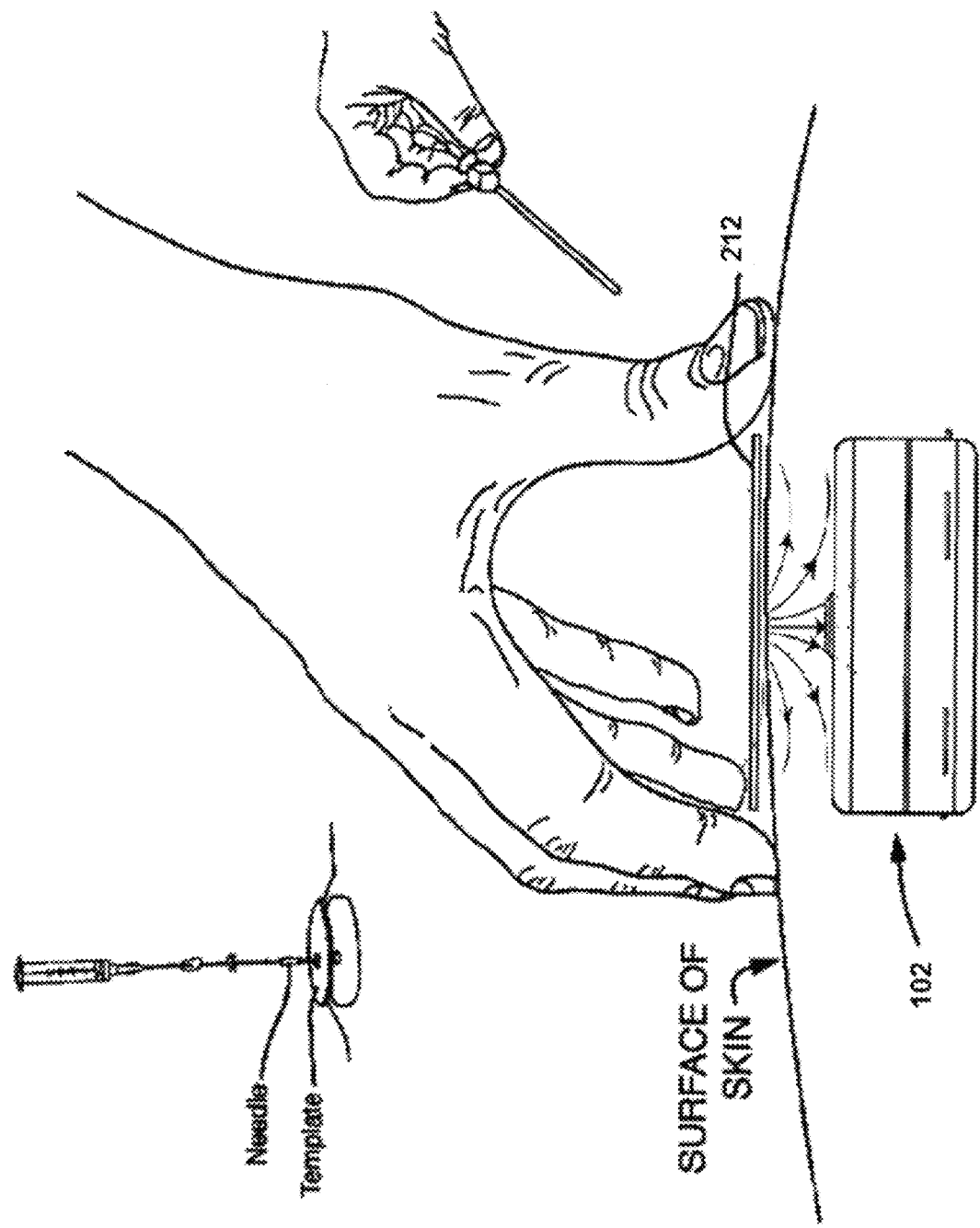
FIG. 8 depicts an interaction between a refill template including one or more magnetic elements and an implanted medical pump, in accordance with an embodiment of the disclosure.

Referring to FIG. 8, an implantable medical pump 102 engaged in a medicament refilling procedure is depicted in accordance with an embodiment of the disclosure. During the refill procedure, the template 212 is orientated with respect to the implantable medical pump 102 and positioned against the patient's skin as an aid in locating the access port 132. As previously described, in some embodiments, the template 212 can include one or more magnetic elements 226 configured to aid in aligning the template 212 with the implantable medical pump 102. In some embodiments, the one or more magnetic elements 226 can serve as a contactless key to either directly or indirectly affect a change in a valve or other mechanism associated with or enabling the medicament refill procedure (e.g., access valve 122). In some embodiments, the computing device 120 (e.g., via a magnetic sensing element 156) can be configured to detect or sense the proper positioning of the one or more magnetic elements 226 or the appropriate response of the implantable medical pump 102 for the purpose of providing feedback to a clinician during the refill procedure. For example, in some embodiments the computing device 120 can be configured to sense a magnetic flux density, field strength or polarity to determine a relative position of the magnetic elements 226 relative to the implantable pump 102 for comparison to an acceptable range of positions of the magnetic elements 226 relative to the implantable pump 102. In some embodiments a visual, audible tone or vibratory response by alarm 133 within the implantable medical pump 102 can be produced to notify the clinician of proper placement or positioning of the magnetic elements 226 and are the appropriate action taken by the implantable medical pump 102 (e.g., movement of access valve 122).

In one embodiment, the processor 121 can be configured to log the date and time of any interaction between the magnetic elements 226 and the implantable medical pump 102 for use in creating a historical log of events or providing user feedback, for example, via the external programmer 108 or server 110. Some embodiments of the present disclosure can be configured to serve as an aid in aligning a timing between physical actions taken during a refill procedure and one or more corresponding virtual steps performed in conjunction with the external programmer 108, for example by utilizing a proper positioning of the template 212 to trigger one or more automated responses within either the implantable medical pump 102 itself or within the external programmer 108.

Figure 9:
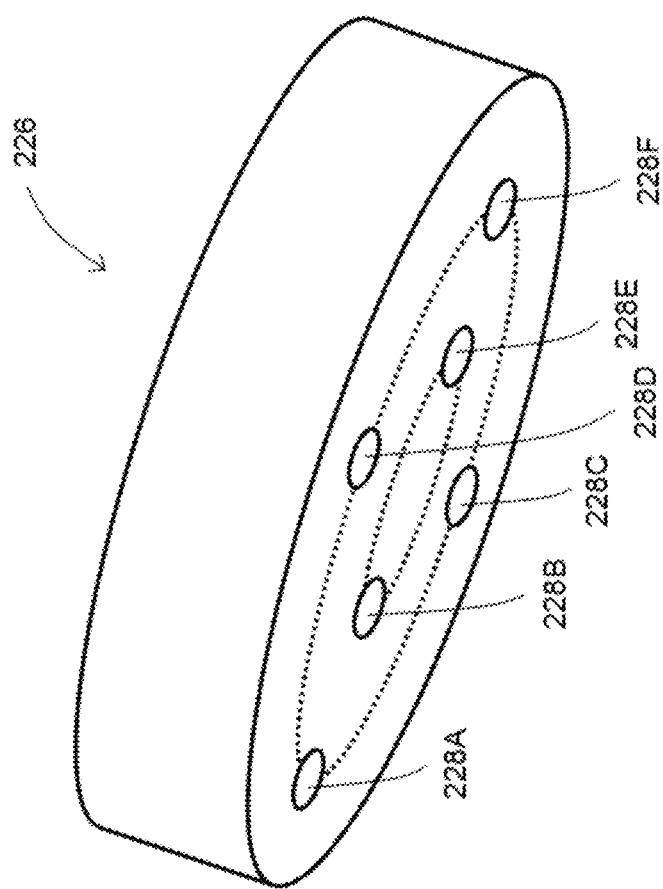
FIG. 9 depicts a coded magnetic key including a plurality of maxels, in accordance with an embodiment of the disclosure.

Referring to FIG. 9, a magnetic element 226 in the form of a coded magnetic key is depicted in accordance with an embodiment of the disclosure. "Coded magnet keys" are magnetic structures formed of multiple individual magnetic elements 228A-F, each of which has both a north and a south pole. Individual magnetic elements 228A-F may vary in terms of which pull faces a surface of a coded magnetic key 226. Thus, a single coded magnet key 226 may have multiple magnetic poles on a single surface, and these multiple magnetic poles may cooperate to form a pattern of north and south poles. The constituent magnetic elements 228A-F may be referred to as "maxels." By properly positioning maxels on a coded magnetic key 226, a force curve having a particular attractive and repulsive strength at certain distances may be created. Generally, the coding of a correlated magnetic key 226 (e.g., the placement of maxels having particular field strengths and polarities) creates a particular two-dimensional pattern on the surface, and thus a three-dimensional magnetic field.

In some embodiments, the coded magnetic key 226 can be programmed or reprogrammed dynamically via a controller by using one or more electromagnetic maxels 228A-F. example, a current applied to the electromagnetic maxels 228A-F can produce a magnetic field. When no voltage is applied, the maxels 228A-F will be magnetically inert. Coded magnetic key patterns may be dynamically switched by using electromagnetic maxels 228A-F, which can switch their polarity as a current is applied. As depicted in FIG. 9, the maxels 228A-F are arranged in a concentric circle configuration, although other quantities of maxels 228A-F and configurations such as a rectilinear array, strips, spirals, helixes, and other geometric shapes are also contemplated. For a given a coded magnet key 226 having a total of six reprogrammable maxels 228A-F, the number of possible configurations equals $3^6$, or 729 possible magnetic key codes at any given moment.

In some examples, coded magnetic key 226 of FIG. 9 may be positioned physically proximate to implantable medical pump 102. Implantable medical pump 102 may determine a coded magnet key 226 based on one or more of electromagnetic maxels 228A-F. If coded magnet key 226 is authenticated and/or authorized by implantable medical pump 102, then implantable medicate pump 102 may manipulate or otherwise configure the access valve into an open position fluidly coupling the medicament reservoir to the access port. If coded magnet key 226 is not authenticated and/or not authorized by implantable medical pump 102, then implantable medicate pump 102 may manipulate or otherwise configure the access valve into a closed position isolating the medicament reservoir from the access port.

Referring to FIG. 10, in some embodiments, the magnetic element or key 226 can be configured as a standalone contactless key, which can be specifically coded to perform a desired function on the implantable medical pump 102, without the involvement of an external programmer 108 or server 110. Accordingly, in some embodiments, the magnetic element 226 can represent a cost-effective alternative to more complicated systems capable of instructing the implantable medical pump 102 to perform one or more advanced functions (e.g., initiate a bolus, temporarily pause medicament delivery, enter MRI safe mode, etc.).

For example, in one embodiment, it is contemplated that emergency room personnel can be provided with one or more contactless magnetic master keys, which when positioned in proximity to the implantable medical pump 102 can be configured to cause the pump 102 to enter into a MRI safe mode, to reduce the risk of a pump malfunction (e.g., overdose) when exposed to a large and varying magnetic field during an MRI or similar such procedure. In some embodiments, the pump 102 can be configured to provide an auditory or vibratory feedback (e.g., via alarm 133) to confirm that the pump 102 has performed the desired action or entered the desired mode. Accordingly, embodiments of the present disclosure enable emergency room personnel to perform limited programming of an implantable medical pump 102 without the complication and expense of an external programmer 108.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable medical pump system configured to selectively permit access to a medicament reservoir by way of at least one contactless key, the implantable medical pump system comprising:
    an implantable medical pump including a medicament reservoir fluidly coupled to an access port via a first conduit, a second conduit and an access valve;
    at least one contactless key configured to impart a magnetic field upon a portion of the implantable medical pump to manipulate the access valve between a first position fluidly coupling the medicament reservoir to the access port via the first conduit, a second position fluidly coupling the medicament reservoir to the access port via the second conduit, and a third position isolating the medicament reservoir from the access port; and
    an access template including at least one magnetic element configured to impart a magnetic field upon a portion of an implanted medical device to urge the access template into a desired position with respect to the implanted medical device to align an access port of the access template with an access port of the implanted medical device, wherein at least one magnetic element of the access template is further configured to impart a magnetic field upon a portion of the implanted medical device to manipulate at least one access valve between a closed position isolating a fluid pathway from the access port of the implanted medical device, and an open position fluidly coupling the fluid pathway to the access port of the implanted medical device.

2. An implantable medical pump system configured to selectively permit access to a medicament reservoir by way of at least one contactless key, the implantable medical pump system comprising:
    an implantable medical pump including a medicament reservoir fluidly coupled to an access port via a first conduit, a second conduit and an access valve;
    at least one contactless key configured to impart a magnetic field upon a portion of the implantable medical pump to manipulate the access valve between a first position fluidly coupling the medicament reservoir to the access port via the first conduit, a second position fluidly coupling the medicament reservoir to the access port via the second conduit, and a third position isolating the medicament reservoir from the access port; and
    an access template including at least one magnetic element configured to impart a magnetic field upon a portion of an implanted medical device to urge the access template into a desired position with respect to the implanted medical device to align an access port of the access template with an access port of the implanted medical device, wherein at least one magnetic element of the access template is further configured to impart a magnetic field sensed by a magnetic field sensing element of the implanted medical device.

3. The implantable medical pump system of claim 2, wherein the access template includes at least two magnetic elements configured for magnetically aligning the access template with the implantable medical device.

4. An implantable medical device access system configured to enable aided alignment of an access template with an implanted medical device, the implantable medical device access system comprising:
    an implantable medical device including an access port, wherein the implantable medical device includes a medicament reservoir fluidly coupled to the access port via one or more conduits including an access valve configured to selectively isolate the medicament reservoir from the access port of the implantable medical device; and
    an implantable medical device access template including at least one magnetic element configured to impart a magnetic field upon a portion of the implantable medical device to urge the access template into a desired position with respect to the implantable medical device to align an access port of the access template with the access port of the implantable medical device, and including at least one contactless key incorporated into the access template and configured to impart a magnetic field upon the access valve to selectively isolate the medicament reservoir from the access port of the implantable medical device.

5. An implantable medical device access system configured to enable aided alignment of an access template with an implanted medical device, the implantable medical device access system comprising:
    an implantable medical device including an access port; and
    an implantable medical device access template including at least one magnetic element configured to impart a magnetic field upon a portion of the implantable medical device to urge the access template into a desired position with respect to the implantable medical device to align an access port of the access template with the access port of the implantable medical device, wherein at least one magnetic element of the access template is configured to impart a magnetic field upon a portion of the implantable medical device to manipulate an access valve between a closed position isolating a medicament reservoir from the access port of the implantable medical device, and an open position fluidly coupling the medicament reservoir to the reservoir to the access port of the implantable medical device.

6. An implantable medical device access system configured to enable aided alignment of an access template with an implanted medical device, the implantable medical device access system comprising:
    an implantable medical device including an access port and a medicament reservoir fluidly coupled to the access port via one or more conduits including at least one access valve configured to selectively isolate the medicament reservoir from the access port;
    an implantable medical device access kit including an access template including at least one magnetic element configured to impart a magnetic field upon a portion of the implantable medical device to urge the access template into a desired position with respect to the implantable medical device to align an access port of the access template with the access port of the implantable medical device, wherein the at least one magnetic element of the access template is configured to impart a magnetic field upon a portion of the implantable medical device to manipulate the at least one access valve between a closed position isolating the medicament reservoir from the access port of the implantable medical device, and an open position fluidly coupling the medicament reservoir to the access port of the implantable medical device, wherein the at least one access valve includes a magnetic element or ferritic portion configured to interact with the at least one magnetic element, thereby enabling the at least one magnetic element to directly manipulate the at least one access valve between the closed position and the open position.

7. The implantable medical device access system of claim 6, wherein the implantable medical device includes a first conduit fluidly coupling the medicament reservoir with the access port of the implantable medical device adapted for refilling of the medicament reservoir, and a second conduit fluidly coupling the medicament reservoir with the access port of the implantable medical device adapted for aspiration of the medicament reservoir.

8. The implantable medical device access system of claim 7, wherein a first access template is configured to selectively open the first conduit, via a first contactless key, and a second contactless key is configured to selectively open the second conduit.

9. The implantable medical device access system of claim 6, further including an implantable pump that includes a magnetic field sensor configured to sense a magnetic field of the at least one magnetic element of the access template.

10. The implantable medical device access system of claim 9, wherein the implantable medical device is configured to provide at least one of an auditory or vibratory feedback response upon proper positioning of the access template relative to the implantable medical device as determined by the magnetic field sensor.

11. The implantable medical device access system of claim 9, wherein the implantable medical device is configured to log a date and time of a sensed presence of the magnetic field of the access template.

12. A method comprising:
providing an access template including at least one magnetic element, the access template configured to be positioned in proximity to an implantable medical device, the implantable medical device including an access port and a medicament reservoir fluidly coupled to the access port via one or more conduits including an access valve configured to selectively isolate the medicament reservoir from the access port;
wherein the at least one magnetic element is configured to impart a magnetic field upon a portion of the implantable medical device to urge the access template into a desired position with respect to the implantable medical device to align an access port of the access template with the access port of the implantable medical device, and wherein at least one magnetic element of the access template is configured to impart a magnetic field upon a portion of the implantable medical device to manipulate the access valve between a closed position isolating the medicament reservoir from the access port of the implantable medical device, and an open position fluidly coupling the medicament reservoir to the access port of the implantable medical device.

* * * * *